United States Patent [19]

Lobdell et al.

[11] 4,205,042
[45] May 27, 1980

[54] BLOOD OXYGENATOR WITH A GAS FILTER

[75] Inventors: Donn D. Lobdell, Golden; Stephen J. Herman, Evergreen; Joel F. Giurtino, Littleton, all of Colo.

[73] Assignee: Cobe Laboratories, Inc., Lakewood, Colo.

[21] Appl. No.: 918,359

[22] Filed: Jun. 23, 1978

[51] Int. Cl.² .............................................. A61M 1/03
[52] U.S. Cl. .................................... 422/47; 55/178; 128/DIG. 3; 422/46; 435/2
[58] Field of Search ................... 422/45-47; 55/178; 128/DIG. 3; 195/1.8

[56] References Cited

U.S. PATENT DOCUMENTS

| | | | |
|---|---|---|---|
| 2,896,620 | 7/1959 | Tremblay | 422/47 |
| 3,049,122 | 8/1962 | Everett | 422/45 |
| 3,769,163 | 10/1973 | Brumfield | 422/45 X |
| 4,033,724 | 7/1977 | Tanoiya | 422/45 |
| 4,065,264 | 12/1977 | Lewin | 422/46 |

FOREIGN PATENT DOCUMENTS

| | | | |
|---|---|---|---|
| 989821 | 9/1951 | France | 422/45 |
| 715612 | 9/1954 | United Kingdom | 422/45 |

Primary Examiner—Michael S. Marcus

[57] ABSTRACT

A blood oxygenator with an oxygen filter in the oxygen inlet chamber, featuring in a particular aspect elevating the filter above the diffuser plug of the oxygenator.

1 Claim, 16 Drawing Figures

BLOOD OXYGENATOR WITH A GAS FILTER

FIELD OF THE INVENTION

This invention relates to gas filters for blood oxygenators.

BACKGROUND OF THE INVENTION

Oxygen and other gases introduced into a blood oxygenator must be filtered to remove impurities before the gases are diffused under pressure through a porous diffuser plug to create bubbles in the blood. Should oxygen pressure be lost during oxygenation, blood can pass through the porous diffuser plug and potentially clog the gas filter. Present oxygen filters are external devices connected upstream of the oxygen inlet to the oxygenator.

SUMMARY OF THE INVENTION

We have discovered that oxygenator performance can be improved and operation simplified by positioning an oxygen filter in the oxygen inlet chamber of an oxygenator rather than as a separate element upstream of the oxygenator. In particular aspects, our invention features elevating the filter above the diffuser plug of the oxygenator, providing a housing for supporting the filter, and providing a filtered oxygen chamber downstream of the filter. The invention minimizes the likelihood of unwanted particulates getting into the oxygen after it leaves the filter and before it enters the blood. In particular aspects, an elevated oxygen filter offers the advantage that if a backup of blood occurs during an oxygen pressure loss, blood contacting the filter will not remain on the filter surface.

PREFERRED EMBODIMENT

The structure and operation of the preferred embodiment of the invention are as follows:

Structure

The drawings show the preferred embodiment and relates apparatus, which are then described.

1. Drawings

2. Description

Figures 1, 2, 3, 4, 5, 6:
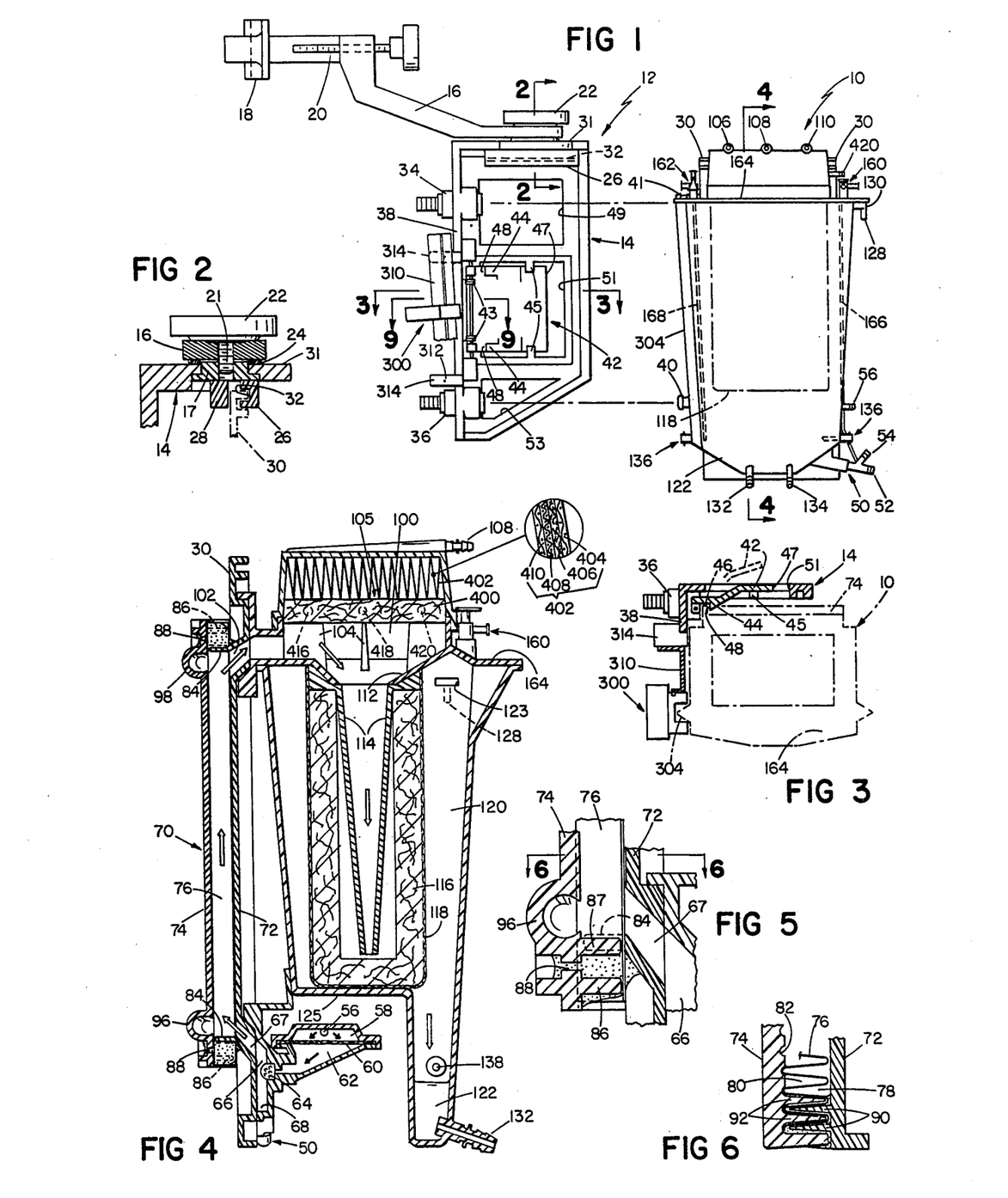
FIG. 1 is an elevation view of said embodiment, showing the blood oxygenator being inserted into its supporting mount (a portion of the mounting plate for a level monitor is cut away)
FIG. 2 is a fragmentary sectional view taken through 2—2 of FIG. 1.
FIG. 3 is a fragmentary sectional view taken through 3—2 of FIG. 1 with the blood oxygenator shown installed in broken lines.
FIG. 4 is a sectional view taken through 4—4 of FIG. 1, showing the blood and oxygen paths through the oxygenator (with the cardiotomy filter shown diagrammatically and a portion enlarged)
FIG. 5 is an enlarged sectional view of the lower back of the oxygenator, showing fingers used in sealing the gas and heat exchange column.
FIG. 6 is a sectional view taken through 6—6 of FIG. 5.

Turning to FIG. 1, there is shown blood oxygenator 10 being inserted into aluminum supporting mount 12. The mount has back brace 14 from which extends arm 16. At the end of arm 16 is formed V-shaped gripping portion 18 which cooperates with screw 20 to grasp a mounting post (not shown). Arm 16 is rotatably fastened to back brace 14 by nylon bearing 17 (FIG. 2), to which the arm is attached by two screws (not shown). Knob 22 turns screw 21 threaded into nylon bearing 17 to squeeze arm 16 and brace 14 against nylon lock washer 24 to lock the arm in any angular position in relation to the brace.

Below the arm-to-brace connection are nylon track portions 26, 28 (FIG. 2), which receive lip 30 on the top of oxygenator 10 and are secured to horizontal shelf 31 on brace 14. Track portion 26 has groove 32. Brass water couplings 34, 36 secured in vertical wall 38 by set screws (not shown) receive plastic inlet fitting 40 and outlet fitting 41 on oxygenator 10. Internal O-rings (not shown) in the brass couplings seal between the couplings and fittings. Back plate 42, which is biased by torsion springs 43 against stops 45 and and which has ramp portions 44 (FIG. 3), captures tab 46 on the back of oxygenator 10 in grooves 48 at the ends of the ramp portions. Openings 49, 51, 53 are provided in the brace. Back plate 42 swings through opening 51 into which stops 45 protrude. Level monitor mounting plate 310 fastened to bosses 314 supports level monitor 300.

Oxygenator 10 is constructed entirely of clear polycarbonate plastic (such as Lexan, a General Electric trademark) except where noted, and individual pieces are adhered by solvent bonding or by a polyurethane adhesive.

Figure 7:
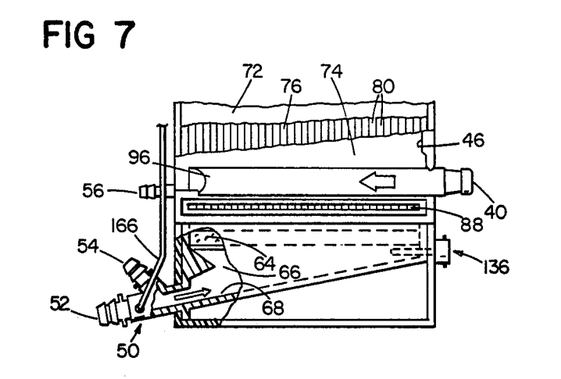
FIG. 7 is a fragmentary elevation view partially cut away, of the lower back of the blood oxygenator.

At the lower right rear of the oxygenator (FIG. 1) is blood inlet fitting 50, which has separate integral barbed fittings 52, 54 for receiving venous and cardiotomy blood, respectively (shown in detail in FIG. 7). Adjacent and slightly above blood inlet fitting 50 is barbed oxygen inlet fitting 56. Oxygen enters chamber 58 (FIG. 4), passes through flat horizontal filter 60 (Gelman Instrument Company, Ann Arbor, Mich., ANH-200, 0.2 micron hydrophobic nylon mesh coated with a polyvinyl chloride-acrylonitrile coating), and through downward sloping chamber 62 to diffuser plug 64 (sold under 3M Company trademark Tegraglas, 40 micron grade, a porous ceramic material), through which it diffuses to form bubbles in the blood in chamber 66. Venous and cardiotomy blood enter chamber 66 and travel upwardly along its sloping lower surface 68 (FIG. 7).

Chamber 66 leads through passage 67 (FIG. 4) into gas and heat exchange column 70 (approximately 6 inches by 12 inches by ⅛ inch) on the back of the oxygenator. The column consists of corrugated stainless steel sheet 76 (0.008 inch thick 304 stainless steel, annealed and polished) (FIG. 6) sandwiched between center plate 72 (blood side) and outside housing 74 (water side). Housing 74 is molded of opaque ABS plastic. Center plate 72 nearly touches (0.000–0.030 inch gap) peaks in the corrugations of sheet 76, and elongated longitudinal grooves 82 in housing 74 receive the corrugations, thereby forming on each side of sheet 76 about 37 isolated narrow vertical passages 78, 80 (⅛ inch by 0.070 inch in cross section tapering to a 0.055 inch diameter at the base of each passage). One of passages 78 is shown in full length in FIG. 4. Helping seal each of the ends of passages 78, 80 are fingers 84 (FIG. 5) extending from center plate 72 and fingers 86, 87 extending from housing 74. At the top and bottom of housing 74, fingers 86, 87 form two horizontal transverse rows, one on either side of transverse slots 88 in housing 74. At the upper and lower ends of housing 72 fingers 84 form a row longitudinally aligned and staggered with fingers 87. The housings are sealed to the long sides of sheet 76 using staggered longitudinal ridges 90, 92 (FIG. 6) on the sides of center plate 72 and housing 74, respectively, the ridges being received by corrugations in sheet 76. Water enters and leaves passages 80 through inlet and outlet fittings 41, 40, which lead into integrally molded semicylindrical manifolds 96, 98.

Figure 8:
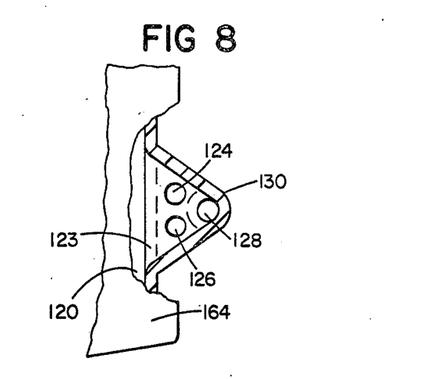
FIG. 8 is a fragmentary plan view, partially cut away, of the blood oxygenator, showing the gas exhaust ports.

Passages 78 (one shown in FIG. 4) on the blood side of corrugated sheet 76 lead into top chamber 100 through passage 102. Ribs 104 are provided in the chamber to support cardiotomy filter 105 used to filter cardiotomy blood returning from the chest incision. Filter 105 comprises a lower reticulated 60 pore per inch Scott Paper Company polyurethane foam sponge 400 treated with Dow Corning Antifoam A surfactant and about ⅛ inch thick, resting on ribs 104, and an upper pleated composite 402 of four layers 404, 406, 408, and 410 (FIG. 4), the layers 404 and 406 being heat sealed to each other at the pleat lines and layers 408 and 410 likewise being heat sealed to each other at the pleat lines. Layers 404 and 410 are DuPont Vexar polypropylene open mesh netting and act as spacers. Layer 406 is made of Remay (DuPont trademark) pressed polyester fibers, and layer 408 is a nylon woven screen having 20 micron pore openings and manufactured by Tetko of Switzerland. Layer 408 has smaller openings than layer 406, which in turn has smaller openings than layers 404 and 410. The pleated composite 402 is compressed within chamber 100 and the open ends of the stack are potted to the chamber with 2-part polyurethane potting (Polyol EP 957 and Vorite 689, a prepolymer, both manufactured by N. L. Industries, Bayonne, N.J., end potting not shown). The pleats are about one inch apart vertically, providing an exposed functional surface area of 750 cm². The combined effect of the four layers is to act as a filter in the 15 to 25 micron range. Cardiotomy blood enters through two of barbed fittings 106, 108, 110 installed in the front wall of chamber 100 and running across the top of chamber 100 to form tapered manifolds. One of the three fittings and manifolds can serve as an infusion port for priming fluid or blood transfusions. Three additional fittings 416, 418, and 420 are positioned along one side wall of chamber 100 for introducing priming solution into the oxygenator. Spacers (not shown) are provided between sponge 400 and the inner ends of the fittings so that the priming solution can bypass the sponge. Ribs 104 extend upward from downward and inward sloping surfaces 112 at the bottom of chamber 100. Surfaces 112 lead into tapered funnel 114, which extends inside of and to within 3/10 inch of the bottom of hollowed out reticulated polyurethane foam sponge 116 (Scott Paper Company, Chester, Pa.) Sponge 116 is treated with Dow Corning Antifoam A (Dow Corning Corporation, Midland, Mich.), a surfactant which assists defoaming of the blood. Surrounding the outside of and giving shape to sponge 116 when under load is stocking 118 made from nylon tricot mesh fabric. Blood emerging from sponge 116 and stocking 118 collects in tapered reservoir 120, which has narrow lower basin 122. Sponge 116 and stocking 118 contact floor 125 of reservoir 120. Gas is exhausted from reservoir 120 through rectangular opening 123 (FIG. 4), which leads to ports 124, 126 (FIG. 8) and tapered fitting 128, all on small triangular-shaped protuberance 130 at the top of the reservoir (FIGS. 1 and 8). At the bottom of reservoir 120 are two blood outlet barbed fittings—arterial return fitting 132 (⅜ inch dia.) and coronary perfusion fitting 134 (¼ inch dia.).

On top surface 164 of the oxygenator are mounted stopcocks 160, 162. Flexible tubing 166 connects the inlet of stopcock 160 with a port in venous inlet fitting 52 (FIG. 7). Tubing 166 travels upward in a channel (not shown) on the outside of reservoir 120 and forward to the stopcock along top surface 164. Rigid plastic tubing 168 connects the inlet of stopcock 162 to a sump (not shown) in the bottom of reservoir 120.

Figure 11:
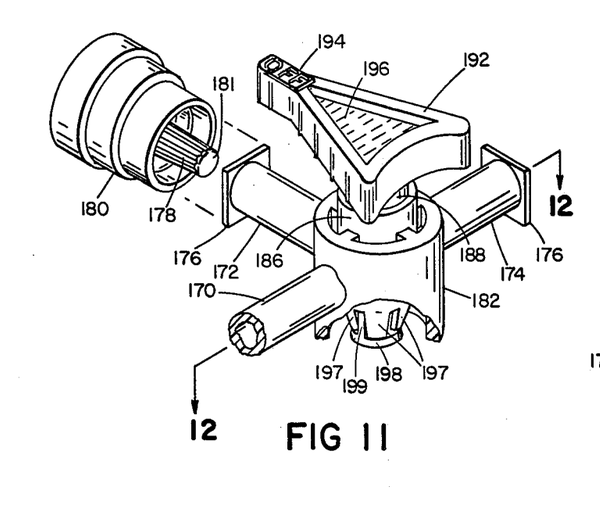
FIG. 11 is an isometric view of a stopcock and cap used on the oxygenator.
Figure 12:
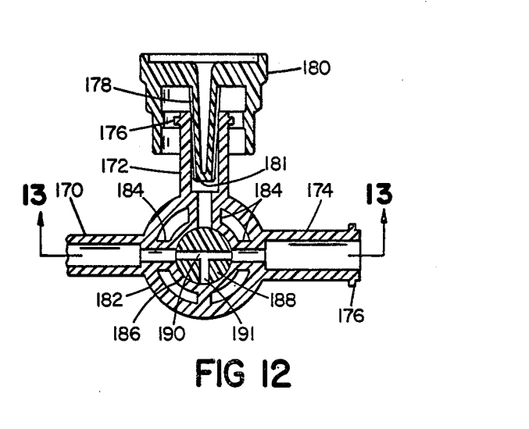
FIG. 12 is a sectional view of the stopcock and cap taken through 12—12 of FIG. 11.
Figure 13:
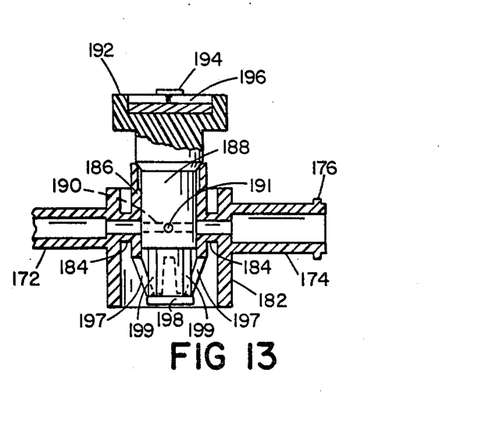
FIG. 13 is a sectional view of the stopcock taken through 13—13 of FIG. 12.

Stopcocks 160, 162 are identical in construction but installed on oxygenator 10 in different orientations. Each stopcock (FIGS. 11, 12, and 13) has an inlet tube 170, which on stopcock 160 extends horizontally and is connected to tubing 166 and which on stopcock 162 extends vertically downward and is connected to tubing 168. Spaced 90° and 180° from inlet tube 170 are outlet fittings 172, 174, each with luer lock fitting 176, which mates with vented cap 180 or with flexible tubing (not shown). Vented cap 180 has grooves 178 in central plug 181 to allow gas to escape. Inlet tube 170 and fittings 172, 174 are integral extensions of cylinder 182. Smaller tubes 184 connect inlet tube 170 and fittings 172, 174 with sleeve 186, all of which are of polycarbonate. Sleeve 186 surrounds core 188 (20% glass filled high density polyethylene). The core has T-shaped passages 190, 191 cut through it communicating between tubes 184. Handle 192 with pointer 194 (labelled "OFF") and colored polystyrene triangular insert 196 is integral with core 188. Pointer 194 extends in a direction 180° from the passage 191. Core 188 is retained in sleeve 186 by four inwardly tapered fingers 197 extending from the bottom of the sleeve and acting against annular lip 198 on the end of the core. Assembly of the stopcock is achieved by simply pushing core 188 down into sleeve 186 until lip 198 snaps past fingers 197. Detent ridges 199 spaced 180° apart extend from the core into the spaces between fingers 197. Dow Corning 360 silicone fluid is used as the lubricant between core 188 and sleeve 186.

Figure 10:
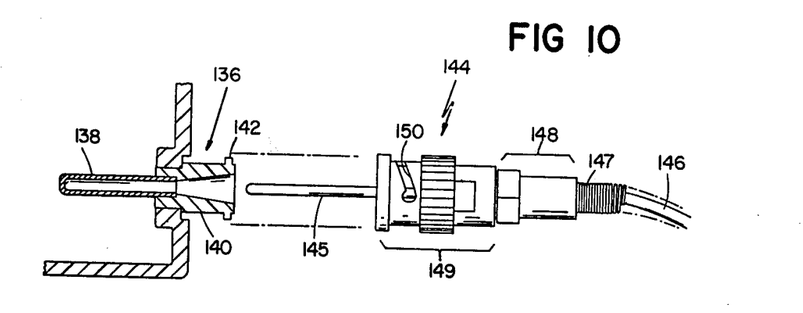
FIG. 10 is a sectional view of a temperature probe and receptacle used on the oxygenator.

Temperature probe receptacles 136, are located in side walls of basin 122 and chamber 66 (FIGS. 1, 7, and 10). Each receptacle consists of a hollow stainless steel tube 138 (FIG. 10), which extends inside basin 122 and chamber 66 and is supported by a molded plastic plug 140 adhesively mounted in the basin and chamber walls and having the external shape of a BNC connector with 180°-spaced protuberances 142. Tubes 138 are closed at their furthest inward ends and open toward the outside at the ends supported in plugs 140. Each temperature-sensitive probe 144 includes a metal probe tip 145, electrical cable 146, and spring sleeve 147 (supplied as a unit under the designation Series 400 by Yellow Springs Instruments, Inc., Yellow Springs, Ohio). The Yellow Springs unit is modified by addition of a nut 148 to which is threaded on a metal BNC connector 149 (Amphenol No. 74868 UG-88/U); the central hole of the BNC is enlarged to receive probe tip 145, and the inner Teflon ring and staked metal ring (not shown) in the BNC are machined down 13/32 inch from the edge of the BNC closest to the probe tip. Each probe tip 145 is inserted through plug 140 into tube 138, so that the end of tip 145 contacts the closed end of tube 138 and is held tightly thereagainst by means of helical slots 150 on the BNC connector receiving protuberances 142 on each plug. Cable 146 connects the probe tip to instrumentation electronics (not shown).

Figure 14:
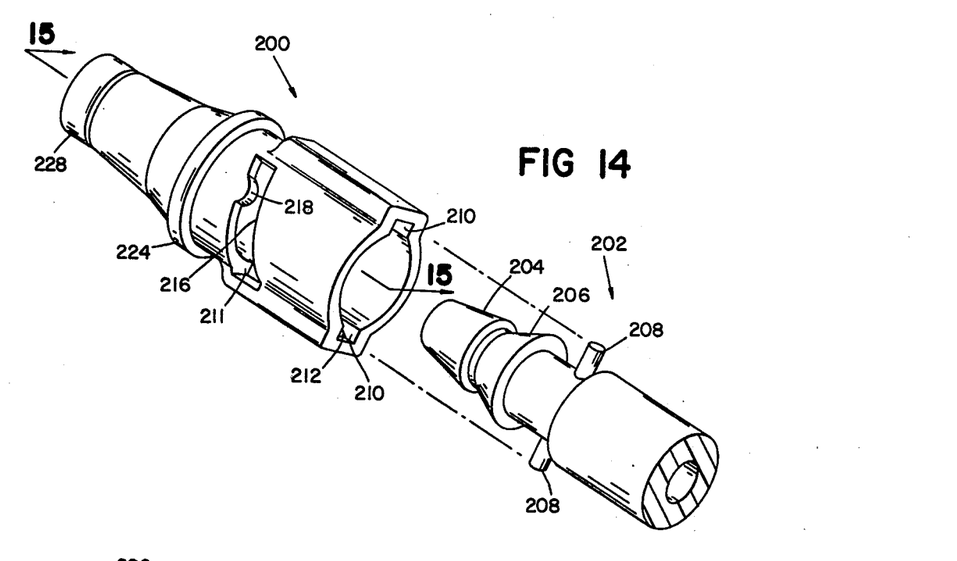
FIG. 14 is an isometric view of a breather cap and fitting used on the oxygenator.
Figure 15:
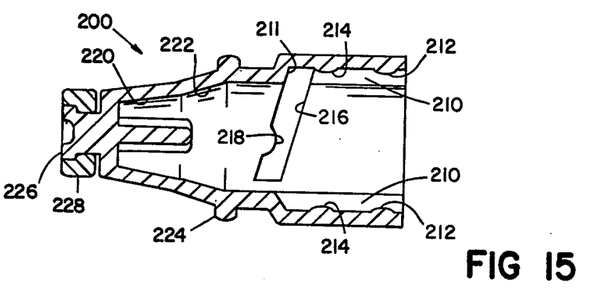
FIG. 15 is a sectional view taken through 15—15 of FIG. 14.

Turning to FIGS. 14 and 15, there is shown a polyethylene breather cap, indicated generally at 200, in position to be mounted on tubular barbed fitting 202 (representative of barbed fittings 52, 54, 56, 106, 108, 110, 132, and 134 on oxygenator 10) shown cut away from the liquid reservoir structure supporting it. Fitting 202 has the conventional frustoconical surfaces 204, 206 ("barbs") designed to accept and tightly engage flexible tubing forced over the fitting, and in back of surfaces 204, 206 it has two cylindrical protuberances 208 spaced 180° apart. Cap 200 has two similarly spaced internal longitudinal grooves 210 which receive protuberances 208 as the cap is slid forward onto fitting 202. Bumps 212 (FIG. 15) at the start of grooves 210 and bumps 214 near the ends of the grooves retard relative backward movement of protuberances 208 in the grooves, providing two positions where the cap is loosely retained on the fitting. Helical slots 216 in the cap directed away from the ends of grooves 210 receive protuberances 208 allowing the cap to be twisted. Raised portions 218 near the ends of the slots retain protuberances 208 locking the cap in a seal position. Frustoconical interior surfaces 220, 222 of the cap mate with exterior surfaces 204, 206 of the fitting in an interference fit because the tapers on the fitting exterior surfaces are more gradual than the tapers on the corresponding interior surfaces of the cap. Protruding ring portion 224 strengthens the cap and facilitates handling. Lipped projection 226 supports colored identification ring 228.

Figure 9:
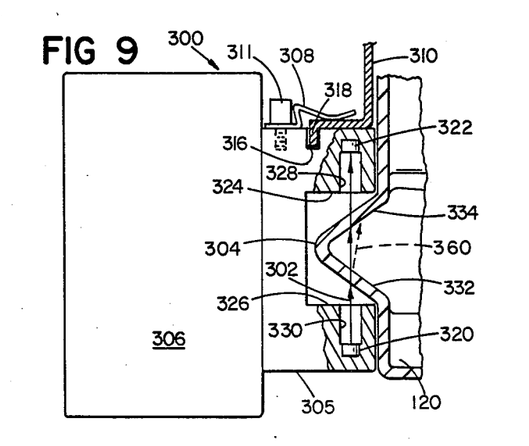
FIG. 9 is a fragmentary sectional view taken through 9—9 of FIG. 1 with the blood oxygenator installed, showing the level monitor.

The level of blood collecting in reservoir 120 is monitored by optical level monitor 300, which passes two parallel, vertically-spaced light beams along paths 302 (both appear as one path in FIG. 9) through vertically-extending protruding ridge 304 (triangular in the sectional view of FIG. 9). The level monitor has U-shaped optics housing 305 (machined polycarbonate) and attached electronics housing 306. Both housings are supported by spring clip 308 tightened against mounting plate 310 by screw 311. The mounting plate is fastened to mount 12 by screws (not shown) received in threaded holes 312 in bosses 314, and is tilted from the vertical to be parallel to ridge 304 (FIG. 1). Groove 316 in optics housing 305 receives lip 318 on the mounting plate.

Vertically-spaced (¾ inch) light emitting diode (LED) sources 320, 321 emit flashing light beams seen by phototransistor sensors 322, 323 (only upper source 320 and upper sensor 322 are shown in FIG. 9). The LED's and phototransistors are recessed ½ inch from surfaces 324, 326 in blind holes 328 and 330 (0.2 inch diameter). Surfaces 324, 326 are spaced 1 inch apart to clear ridge 304, which is ⅜ inch wide at its base, and has 0.10 inch thick equal-length walls 332, 334 angled 55° from the reservoir wall.

Figure 16:
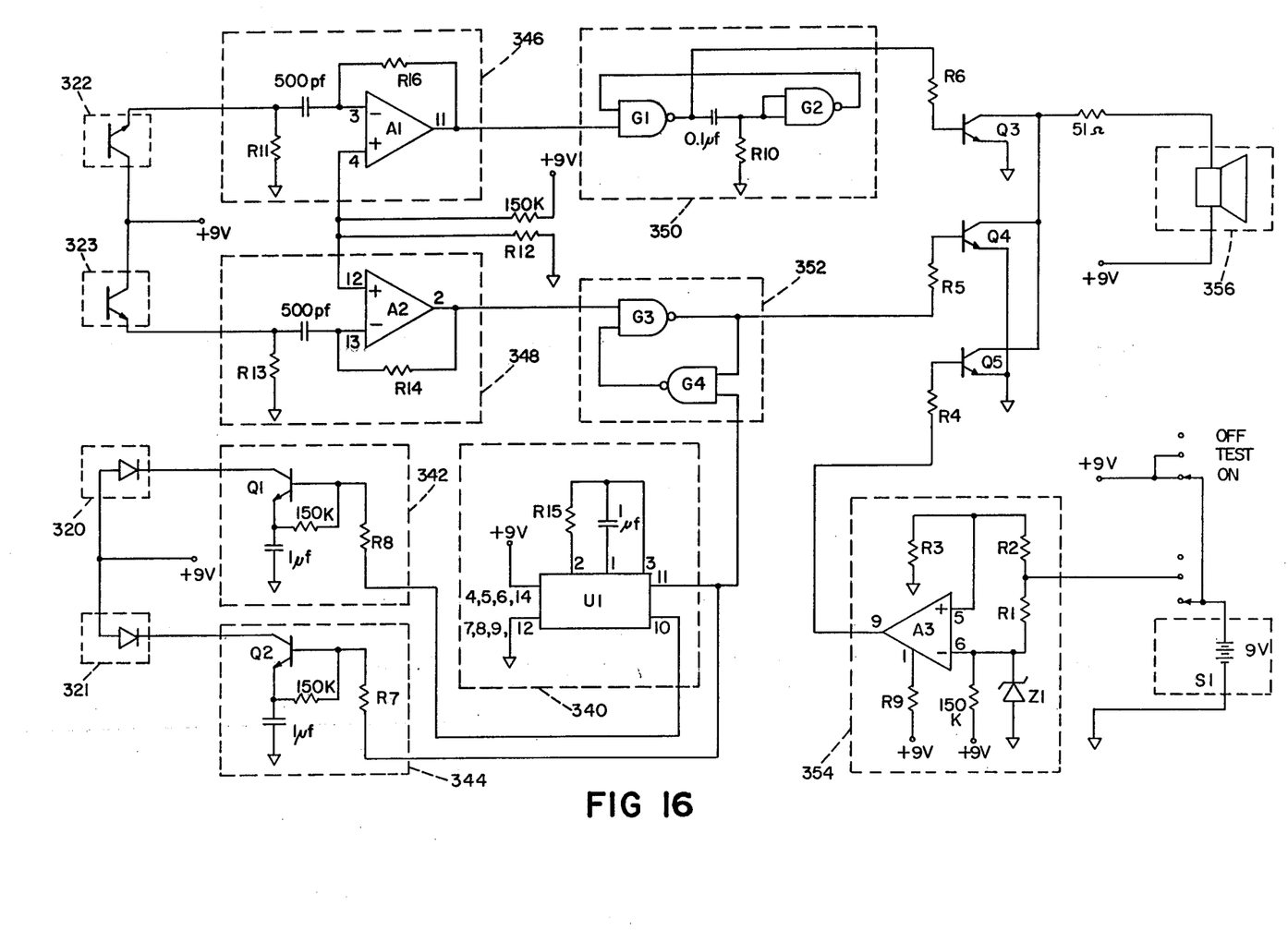
FIG. 16 is a schematic view of the level monitor electronics.

Turning to FIG. 16, there is shown a schematic for the level monitor electronics. Multivibrator 340 generates a pair of 4 hertz square wave outputs which are supplied to transistor stages 342, 344, which drive upper and lower LED sources 320, 321 (OP132W, Optron Incorporated, Carrollton, Tex.) with exponentially decaying current pulses about 10 milliseconds long. Light reaching upper and lower phototransistor sensors 322, 323 (OP803, Optron Incorporated, Carrollton, Tex.) sends an input signal to AC-coupled amplifiers 346, 348, respectively. The output of amplifier 346 controls one-shot flip-flop 350; the output of amplifier 348 cooperates with an output of multivibrator 340 to control set/reset flip-flop 352. Outputs of the two flip-flops and an output from battery level sense circuit 354 drive 400 Hertz audio alarm 356 (AI105, Projects Unlimited, Dayton, Ohio) through power transistors Q3, Q4, Q5. The low frequency of the alarm helps in localizing the oxygenator as the source of the noise in an operating room.

The following table identifies the circuit components shown in FIG. 16, except for those resistors and capacitors whose values are given in the Figure:

Component Table

| | |
|---|---|
| A1-A3 | Siliconix L144CJ |
| G1-G4 | Motorola MC14011 |
| U1 | RCA CD4047 astable multivibrator |
| Q1-Q5 | National Semiconductor LM3086 |
| R1-R8 | Allen Bradley 316B242 (2.4k ohm) |
| R9-R16 | Allen Bradley 316B105 (1M ohm) |
| Z1 | 1N746 Zener diode |
| S1 | Mallory MN1604 (9 V) battery |

To assemble the gas and heat exchange column 70, corrugated sheet 76 is adhered to housing 74 using two-part polyurethane potting applied in grooves 82 and along each side and end of sheet 76. Sheet 76 is then laid into housing 74, the sheet and housing are turned over and placed in a clamping fixture which squeezes them together, and more potting is poured into slots 88. The finished assembly of housing 74 and sheet 76 is then sealed to center plate 72 along plate ridges 92 (using blood-compatible Vorite 689 and Polyol EP 957, two-part polyurethane adhesives of N. L. Industries, Bayonne, N.J.; Vitel 207F primer, a Goodyear Chemicals polyester solution resin, on the blood site of sheet 76; and Alpha 1059 (N. L. Industries) primer on the surface of housing 72, all applied at room temperature), which is bonded to the rest of the oxygenator. Further detail on the procedure for sealing between sheet 76 and housing 74 can be found in the copending U.S. patent application of Joel F. Giurtino and Robert L. Anderson entitled "Leakproof Adhesive Sealing," hereby incorporated by reference.

The oxygenator is used in connection with a heart-lung machine (such as those available from Stockert Instruments, Munich, Germany) which includes blood pumps, a gas flow meter, and a blood pressure monitor. Mount 12 is secured to the heart-lung machine.

Operation

As depicted in FIGS. 1, 2, and 3, oxygenator 10 (a disposable unit) is installed in supporting mount 12 by inserting lip 30, which is along the top of gas and heat exchange housing 70, into the track formed by track portions 26, 28 on mount 12. As the oxygenator is slid sideways, tab 46 protruding from the left rear corner of water housing 74 rides up on ramp portions 44, momentarily rotating back plate 42 backward (to the position shown by dashed lines in FIG. 3). The back plate snaps back into its normal position resting against stops 45 when tab 46 reaches and is received by groove 48, thereby locking the oxygenator in place. Removal of the oxygenator is accomplished by manually rotating back plate 42 backward by pulling on free end 47. Water inlet and outlet fittings 40, 41 are received by an internally sealed to couplings 36, 34. Most of the vertical support for the oxygenator comes from the couplings, the remainder from track portion 26. Tubing (not shown) carrying temperature-controlled water is connected to water inlet fitting 40. Water output is carried away in tubing connected to water outlet fitting 41. Before the oxygenator is used, sterilizing gases are introduced and allowed to breathe out through breather caps 200 and vented caps 180 installed on the various fittings. At the time the oxygenator is to be used a saline priming solution is introduced through one of ports 416, 418, 420, and operation of the level monitor is checked.

To begin oxygenation, venous blood from a catheter or other source is supplied to the oxygenator (at a rate of approximately 5 liters per minute) by a tube (not shown) connected to barbed fitting 52. If cardiotomy blood emanating from the chest incision in the patient is to be supplied to the oxygenator, it is connected using a tube (not shown) connected either to barbed fitting 54 or to two of barbed fittings 106, 108, 110 in top chamber 100, where the cardiotomy blood is filtered in filter 105 resting on ribs 104. If fitting 54 is used, the cardiotomy blood is usually filtered externally. Oxygenated blood is drawn out of the oxygenator through tubes (not shown) connected to barbed fittings 132, 134. A tube connected to fitting 132 supplies blood to the arteries; another connected to fitting 134 supplies blood for direct coronary perfusion. The oxygenator is normally located below the patient, giving a static head to entering blood (patient normally at 40 inches above floor; venous inlet fitting 52 at between 2 and 20 inches above floor).

Oxygen (or a mixture of oxygen and small percentages of either carbon dioxide and/or anesthesia) is supplied under 2 to 5 psi pressure through a tube (not shown) connected to barbed fitting 56. Exhaust gases—unused oxygen and released carbon dioxide—are exhausted through ports 124, 126 and may be drawn off under vacuum through a tube (not shown) connected to tapered fitting 128. Drawing the exhaust gases off in a tube is advantageous in preventing contamination of the operating room atmosphere with anesthesia gases introduced in the gas supplied to the oxygenator.

Gas entering through fitting 56 is filtered by filter material 60 to remove impurities. Filter material 60 is hydrophobic and thus not susceptible to wetting out on contact with liquid. The integral gas filter is elevated above diffuser plug 64 to allow for gravity return through the diffuser and away from the filter surface of blood or priming solution accidentally ingested through the diffuser during a loss of gas flow. If not placed above the diffuser plug, the filter will tend to stay partially blocked by blood after gas flow is reestablished.

Gas diffuses through the many tiny holes in plug 64 and creates bubbles in the blood passing by the plug. Sloping surface 68 (FIG. 7) in chamber 66 helps assure a uniform distribution of incoming blood across the plug.

The blood foam rises from chamber 66 through passage 67 and into individual narrow vertical passages 78 formed by the corrugations in sheet 76. Residence time for bubbles in passages 78 averages approximately 2 seconds at the 5 liter per minute blood flow rate. Bubbles of varying size formed in chamber 66 are shaped into more uniform sizes as they enter passages 78 and are maintained in size as they rise in the columns. Uniformity in bubble size is helpful to achieving uniformity in the rates at which oxygen and carbon dioxide diffuse into and out of the blood. Providing narrow passages for gas diffusion reduces the swirling and stagnation of bubbles that occurs with larger passages.

Simultaneously with gas exchange taking place in passages 78, heat is echanged across sheet 76 between the foamed blood and the water being circulated between sheet 76 and housing 74. Water enters at fitting 40 and travels upward in passages 80 until exiting at outlet fitting 41. Initially entrapped air in passages 80 leaves with the water through fitting 41.

Blood foam leaves vertical passages 78 at passage 102, enters top chamber 100, and then travels down sloping surfaces 112 into funnel 114. Cardiotomy blood filtered through filter 105 joins the main blood flow here. At the bottom of the funnel the foam works back upward outside the funnel and comes in contact with surfactant treated reticulated foam sponge 116 which with the aid of stocking 118 breaks the bubbles. Gas exchange continues to take place in funnel 114. Gas emerging from the burst bubbles escapes through the sponge and is exhausted through ports 124, 126 and fitting 128. Blood collects in reservoir 120 and lower basin 122. Blood volume markings (not shown) in cubic centimeters (50–4000 cc) are applied as decals along the left front face of reservoir 120.

Venous and oxygenated blood samples can be withdrawn from the oxygenator and drugs introduced into the blood through outlet fittings 172, 174 of stopcocks 160, 162. When neither of these operations is taking place, vented caps 180 are left installed on outlet fittings 172, 174, and during sterilization and shipping of the oxygenator, vented caps 180 are installed on the fittings. Caps 180 fit tightly but leave a breathing path for gas through grooves 181. To operate the stopcock, pointer 194 (FIG. 11) is rotated to whichever of the two outlet fittings is not being used.

Temperature probe receptacles 136 provide points to monitor blood temperature before and after the heat exchange. Each temperature-sensitive probe tip 145 fits tightly against the closed end of each hollow metal tube 138, because BNC connector 149 is spring-biased to provide a tight fit, thereby providing good heat transfer characteristics between the blood and probe tip.

Breather cap 200 is installed on barbed fitting 202 (and on other barbed fittings) with protuberances 208 sliding into grooves 210 until reaching ends 211 of the grooves, where bumps 214 retain the cap loosely. In this loose fit position gases are allowed to escape from the reservoir, passing through the annular space between unengaged surfaces 204, 206 and surfaces 220, 222 and leaving the cap along a variety of paths including through slots 216. When the cap is installed on medical devices such as the oxygenator, the loose fit position is used to vent sterilizing gases passed through the reservoir on which fitting 202 is secured. And the position is used whenever it is necessary to bleed gases entrapped in the fitting when liquids are introduced into reservoirs.

To seal the cap to the fitting, the cap is pressed on and then twisted clockwise. Protuberances 208 follow helical slots 216 moving the cap toward the fitting and tightly engaging surfaces 220, 222 against surfaces 204, 206. The mechanical advantage provided by slots 216 working against protuberances 208 in a screwing action facilitates the tight engagement. Raised portions 218 retain the protuberances, locking the cap in the sealed position. The loose breathing position would be used during sterilized shipping of the oxygenator to allow sterilizing gases to escape when the oxygenator is sterilized inside its shipping carton, to protect the fitting and packaging, and to provide a tortuous incoming path for bacteria. The sealed position would be used during operation of the oxygenator to seal in fluids or gases when a particular fitting is not fitted with tubing. E.g., when cardiotomy blood is not returned to the oxygenator, fittings 106, 108, 110, and 54 would have breather caps installed in the sealed position.

The electronics shown in FIG. 16 provides an audible alarm whenever the fluid level (blood or saline priming solution) falls below the level at which level monitor 300 is set. The vertical position of the monitor can be manually adjusted by sliding housings 305, 306 vertically on mounting plate 310. Friction between clip 308 and mounting plate 310 retains the housings at any selected vertical position, and lip 318 and groove 316 guide the housings during adjustment.

A drop in fluid level below the monitor level is sensed by a rise in the intensity of light seen by phototransistor sensors 322, 323. When the intensity rises to 5 percent of the maximum intensity (the intensity achieved when light passes through a clean dry portion of ridge 304), amplifiers 346, 348 generate an output which causes flip-flops 350, 352 to activate 400 Hertz audio alarm 356. As the fluid level drops, upper sensor 322 is the first to sense the rise in light intensity, and it causes a 4 Hertz chirping of the 400 Hz alarm. If the fluid level drops further to below lower sensor 323, the alarm sound becomes an intermittent 400 Hertz tone.

Contamination of the interior surfaces of walls 332, 334 with either a thin film of blood or water condensation can reduce light transmission to 10 percent of maximum intensity, but will still trigger the alarm. However, if blood is allowed to dry on walls 332, 334 in the region monitored, enough light from both LED sources 320, 321 can conceivably be blocked by individual dried drops of blood to cause the monitor to malfunction. Providing two vertically spaced pairs of sources and sensors reduces the likelihood of this occurrence and also provides component redundancy to improve reliability.

When blood fills ridge 304 above the monitoring level, all light generated by the LED sources is absorbed. But when clear priming liquid is above the monitoring level, light refraction, rather than absorption, is relied on to extinguish the light intensity at sensors 322, 323. Light is refracted generally along paths 360, away from the sensors. Light leaving sources 320, 321 along paths 302 is bent inward 10° by the difference in refractivity between air and the priming solution (some bending of the light also occurs in walls 332, 334). The refracted beam strikes wall 334 at a 45° angle and is bent a further 25°, leaving ridge 304 along a path bent inward 35°. Light paths 302, 360 represent the paths of perfectly collimated light emitted by LED sources 320, 321. Because the sources actually emit light in a cone, there being a 50% reduction in light intensity at 12° off axis, some light follows different paths from those shown. Some light undergoes total internal reflection and never exits from wall 334, but enough reaches sensors 322, 323 to produce about 1 percent of maximum intensity there, well below, however, the 5 percent threshold for turning on the alarm.

Other Inventions

Subject matter disclosed herein relating to the level monitor was the joint invention of Donn D. Lobdell, Thomas E. Goyne, Stephen J. Herman, and Robert Anderson, and is the subject of copending U.S. patent application Ser. No. 917,850, filed June 22, 1978.

Subject matter disclosed herein relating to the temperature probe was the joint invention of Donn D. Lobdell, Stephen J. Herman, and Robert Anderson and is the subject of copending U.S. patent application Ser. No. 917,469, filed June 21, 1978.

Subject matter disclosed herein relating to gas exchange using a corrugated column was the joint invention of Donn D. Lobdell and Stephen J. Herman and is the subject of copending U.S. patent application Ser. No. 917,350, filed June 20, 1978.

Subject matter disclosed herein relating to the mount for the oxygenator was the joint invention of Thomas E. Goyne, Stephen J. Herman, Joel F. Giurtino and Robert Anderson and is the subject of copending U.S. patent application Ser. No. 918,360, filed June 23, 1978.

Subject matter disclosed herein relating to the breather cap was the joint invention of Stephen J. Herman and Joel F. Giurtino and is the subject of copending U.S. patent application Ser. No. 918,725, filed June 26, 1978.

Subject matter disclosed herein relating to the stopcock was the invention of Donn D. Lobdell and Joel F. Giurtino and is the subject of copending U.S. patent application Ser. No. 938,250, filed Aug. 30, 1978 and U.S. patent application Ser. No. 937,851, filed Aug. 29, 1978.

Subject matter disclosed herein relating to the transverse openings for sealing the corrugated sheet to the water housing was the joint invention of Joel F. Giurtino and Robert L. Anderson and is the subject of copending U.S. patent application Ser. No. 916,775, filed June 19, 1978.

Incorporation by Reference

We incorporate by reference the copending U.S. patent application of Joel F. Giurtino and Robert Anderson entitled "Leakproof Adhesive Sealing."

What is claimed is:

1. A blood oxygenator comprising:
   a venous blood inlet chamber comprised of a first plastic housing and a venous blood inlet means connected thereto,
   bubble generating means for forming oxygen bubbles in the blood in said blood inlet chamber, said means including a porous member positioned along one wall of said inlet chamber,
   a gas exchange column means extending upwardly above said blood inlet chamber for transporting said bubbles while gas is exchanged with the blood, said column comprising a second plastic housing fastened to said housing forming said blood inlet chamber, defoaming means connected to and communicating with the outlet of said gas exchange means for breaking up said bubbles, blood reservoir means connected to and below said defoaming means for collecting oxygenated blood, said reservoir means and defoaming means comprising a third plastic housing fastened to said exchange column, and oxygen filtering means, comprising a fourth plastic housing fastened to at least one of said other plastic housings, said fourth housing comprising upper and lower plastic members each with mating flanges, an oxygen inlet means secured to said upper member for introduction of oxygen into said fourth housing, oxygen outlet means secured to said lower member, and a filter element in the form of a sheet of hydrophobic material, the thickness of said sheet being substantially less than the transverse dimensions of said sheet, said sheet being positioned completely above said porous member of said bubble generating means to allow for gravity return through said porous member of said bubble generating means and away from the surface of said filter of blood or priming solution accidentally ingested through said porous member of said bubble generating means during a loss of oxygen flow and bonded at its periphery between said mating flanges of said upper and lower members, thereby dividing said housing into upper and lower chambers, said oxygen outlet means being connected to and communicating with said porous member of said bubble generating means.

* * * * *